(12) United States Patent
Shimazu et al.

(10) Patent No.: US 11,813,097 B2
(45) Date of Patent: Nov. 14, 2023

(54) COMPRESSION TUBE ATTACHING-DETACHING UNIT

(71) Applicant: Shimadzu Corporation, Kyoto (JP)

(72) Inventors: Keisuke Shimazu, Kyoto (JP);
Shinsuke Kanazawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 304 days.

(21) Appl. No.: 17/287,395

(22) PCT Filed: Oct. 25, 2018

(86) PCT No.: PCT/JP2018/039635
§ 371 (c)(1),
(2) Date: Apr. 21, 2021

(87) PCT Pub. No.: WO2020/084730
PCT Pub. Date: Apr. 30, 2020

(65) Prior Publication Data
US 2021/0401389 A1 Dec. 30, 2021

(51) Int. Cl.
*A61B 6/00* (2006.01)
(52) U.S. Cl.
CPC .......... *A61B 6/4458* (2013.01); *A61B 6/4482* (2013.01); *A61B 6/487* (2013.01)
(58) Field of Classification Search
CPC ..... A61B 6/4458; A61B 6/487; A61B 6/4482; A61B 6/04; A61B 6/0407; A61B 6/0414; A61B 6/0421
See application file for complete search history.

(56) References Cited

U.S. PATENT DOCUMENTS

| | | | | | |
|---|---|---|---|---|---|
| 3,991,317 | A | * | 11/1976 | Kunne | A61B 6/00 378/173 |
| 6,027,247 | A | * | 2/2000 | Tachi | A61B 6/467 378/177 |
| 2011/0170671 | A1 | * | 7/2011 | Blyakher | A61B 6/0421 378/208 |
| 2012/0011653 | A1 | * | 1/2012 | Coppens | A61N 5/1049 5/601 |

(Continued)

FOREIGN PATENT DOCUMENTS

| | | | | |
|---|---|---|---|---|
| JP | H0658914 U | * | 8/1994 | A61B 6/04 |
| JP | 2000-166915 A | | 6/2000 | |

OTHER PUBLICATIONS

Machine translation of JP-H0658914 (Year: 1994).*

(Continued)

*Primary Examiner* — Dani Fox
*Assistant Examiner* — Soorena Kefayati
(74) *Attorney, Agent, or Firm* — Muir Patent Law, PLLC

(57) ABSTRACT

A compression tube attaching-detaching unit is provided with an arm, a connecting pin, and an attaching-detaching mechanism portion. The arm supports a compression tube. The attaching-detaching mechanism portion is removably coupled with the connecting pin to mount the arm on a radiographic fluoroscopic imaging apparatus. The connecting pin has a shaft portion and a flange portion positioned at the tip end of the shaft portion. The attaching-detaching mechanism portion includes a main body, a lid portion, a locking portion, and an unlocking portion.

5 Claims, 11 Drawing Sheets

(56) References Cited

U.S. PATENT DOCUMENTS

| | | | | |
|---|---|---|---|---|
| 2012/0257724 A1* | 10/2012 | Nakamura | ........... | A61B 6/0414 |
| | | | | 378/189 |
| 2012/0269328 A1* | 10/2012 | Guo | .................... | A61B 6/4458 |
| | | | | 378/208 |
| 2017/0340303 A1* | 11/2017 | Stango | ................... | A61B 90/17 |

OTHER PUBLICATIONS

Written Opinion by the International Search Authority for PCT application No. PCT/JP2018/039635 dated Jan. 29, 2019, submitted with a partial machine translation.

* cited by examiner

COMPRESSION TUBE ATTACHING-DETACHING UNIT

TECHNICAL FIELD

The present invention relates to a compression tube attaching-detaching unit.

BACKGROUND OF THE INVENTION

As a prior art document disclosing a structure of a radiographic fluoroscopic imaging apparatus having a compression mechanism, there is Japanese Unexamined Patent Application Publication No. 2000-166915 (Patent Document 1). The compression mechanism of the radiographic fluoroscopic imaging apparatus described in Patent Document 1 includes a guide, a tubular bracket, a support rod, an operation grip, and a compression tube. The guide is provided on the X-ray imaging system. The tubular bracket slides on the guide upward and downward. The support rod is vertically attached to the cylindrical bracket. The operation grip is provided at the tip end of the support rod. The compression tube is provided at the intermediate portion of the support rod.

PRIOR ART DOCUMENT

Patent Document

Patent Document 1: Japanese Unexamined Patent Application Publication No. 2000-166915

SUMMARY OF THE INVENTION

Problems to be Solved by the Invention

The compression tube is sometimes removed from the fluoroscopic imaging apparatus when the compression tube is not in use. In a conventional fluoroscopic imaging apparatus, the operation for attaching and detaching a compression tube is complicated.

The present invention has been made in view of the above-described problems, and an object thereof is to provide a compression tube attaching-detaching unit capable of easily attaching and detaching a compression tube.

Means for Solving the Problem

A compression tube attaching-detaching unit based on the present invention is provided with an arm, a connecting pin, and an attaching-detaching mechanism portion. The arm supports a compression tube. The attaching-detaching mechanism portion mounts the arm on a radiographic fluoroscopic imaging apparatus by being detachably coupled with the connecting pin. The connecting pin has a shaft portion and a flange portion positioned at the tip end of the shaft portion. The attaching-detaching mechanism portion includes a main body, a lid portion, a locking portion, and an unlocking portion. The main body has a groove portion into which the flange portion is relatively slidably inserted. The lid portion has a cut-out portion into which the shaft portion is relatively slidably inserted, the lid portion being fixed to the main body to accommodate the flange portion between the lid portion and the main body. The locking portion is attached to the main body to be positioned on a slide insertion path of the flange portion, the locking portion being provided so as to be contactable and separatable with respect to the lid portion and being configured to receive a biasing force in a direction approaching the lid portion. The unlocking portion is attached to the main body, the unlocking portion being configured to separate the locking portion from the lid portion against the biasing force. At a lid portion side tip end of the locking portion, an inclined surface that comes into slide contact with the flange portion to be slidably inserted is provided. The inclined surface is inclined to be positioned in a slide insertion direction of the flange portion as the inclined surface advances toward the lid portion tip end of the locking portion.

With this, it is possible to easily attach and detach the connecting pin to the attaching-detaching mechanism portion. Thus, it is possible to easily attach and detach the compression tube.

According to one embodiment of the present invention, the shaft portion and the flange portion each have a cylindrical outer shape.

With this, in any direction of 360°, it is possible to couple the connecting pin with the attaching-detecting mechanism portion by slidably moving the connecting pin in a direction relatively approaching the attaching-detaching mechanism portion.

According to one embodiment of the present invention, the arm is rotatable via the attaching-detaching mechanism portion about the connecting pin as a rotating shaft.

This allows the compression tube to be easily moved between the inside of the X-ray field of view and the outside of the X-ray field of view of the imaging system.

According to one embodiment of the present invention, at an end portion of the arm opposite to an attaching-detaching mechanism portion side of the arm, an operation grip for manually rotating the compression tube is provided.

With this, the force for pressing the compression tube against the imaging target can be finely adjusted as compared with the case in which motor power assist is used. As a result, it is possible to prevent application of an excessive pressing force to the compression tube.

According to one embodiment of the present invention, the attaching-detaching mechanism portion further includes an elastic body. The elastic body is attached to the main body to be positioned within the groove portion. The elastic body is configured to bias the flange portion accommodated between the main body and the lid portion toward the lid portion.

With this, the connecting pin can be stably connected to the attaching-detaching mechanism portion. As a result, it becomes possible to stably support the compression tube.

Effects of the Invention

According to the present invention, the compression tube can be easily attached and detached.

EMBODIMENTS FOR CARRYING OUT THE INVENTION

Figure 1:
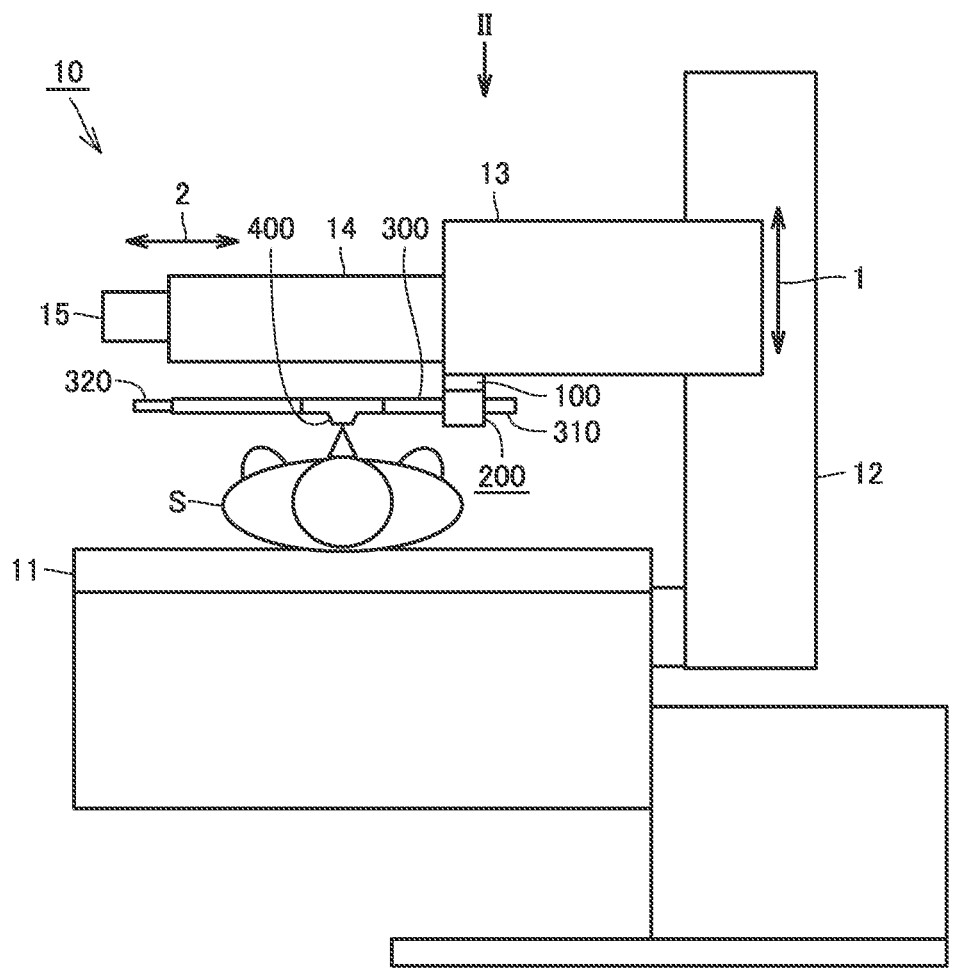
FIG. 1 is a side view showing the configuration of a radiographic fluoroscopic imaging apparatus including a compression tube attaching-detaching unit according to one embodiment of the present invention.

Hereinafter, a radiographic fluoroscopic imaging apparatus including the compression tube attaching-detaching unit according to one embodiment of the present invention will be described. In the following description of the embodiment, the same or corresponding component in the drawings is denoted by the same reference numeral, and the description thereof will not be repeated.

Figure 2:
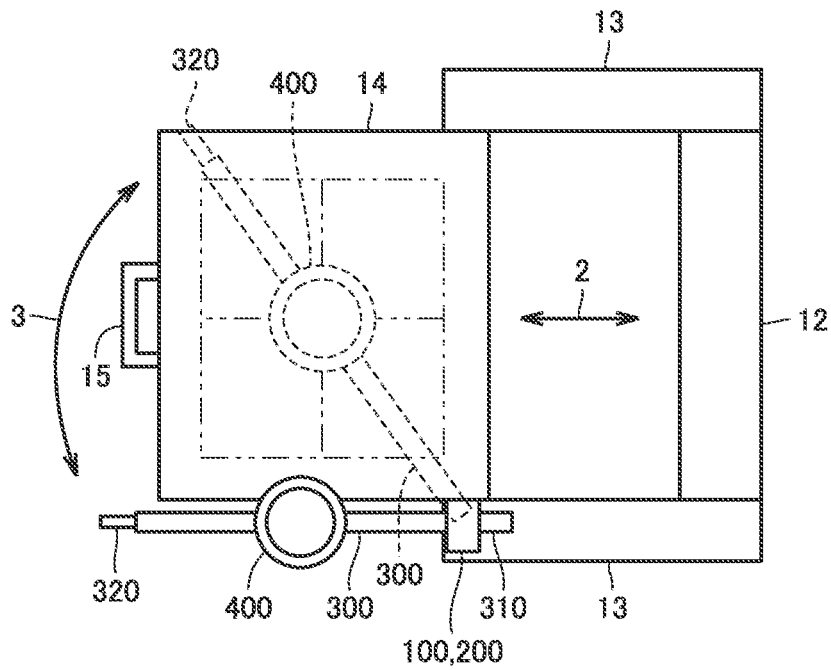
FIG. 2 is a plan view of the radiographic fluoroscopic imaging apparatus of FIG. 1 as viewed in the direction of the arrow II.

FIG. 1 is a side view showing a configuration of a radiographic fluoroscopic imaging apparatus including a compression tube attaching-detaching unit according to one embodiment of the present invention. FIG. 2 is a plan view of the radiographic fluoroscopic imaging apparatus of FIG. 1 as viewed from the arrow II direction. In FIG. 1 and FIG. 2, the state in which the compression tube is positioned at the outer side of the X-ray field of view is illustrated by a solid line.

As shown in FIGS. 1 and 2, the radiographic fluoroscopic imaging apparatus 10 including the compression tube attaching-detaching unit according to one embodiment of the present invention includes a bed 11, a support portion 12, a flame 13, an imaging system 14, an operation handle 15, and a compression tube attaching-detaching unit.

The radiographic fluoroscopic imaging apparatus 10 irradiates an imaging target S on the bed 11 with X-rays to perform fluoroscopic imaging. An X-ray tube is arranged inside the bed 11. The support portion 12 extends upward from the side of the bed 11. The flame 13 is mounted movable in the up-down direction indicated by the arrow 1 with respect to the support portion 12. The imaging system 14 has an X-ray field of view as shown by a two-dot chain line in FIG. 2.

On a side of the imaging system 14 opposite to the support portion 12 side, an operation handle 15 is attached. The imaging system 14 is movably attached to the flame 13 in the left-right direction indicated by the arrow 2. The imaging system 14 is equipped with a function that detects the force applied to the operation handle 15 to power-assist each of the vertical and longitudinal movements of the imaging system 14 by a motor.

Figure 3:
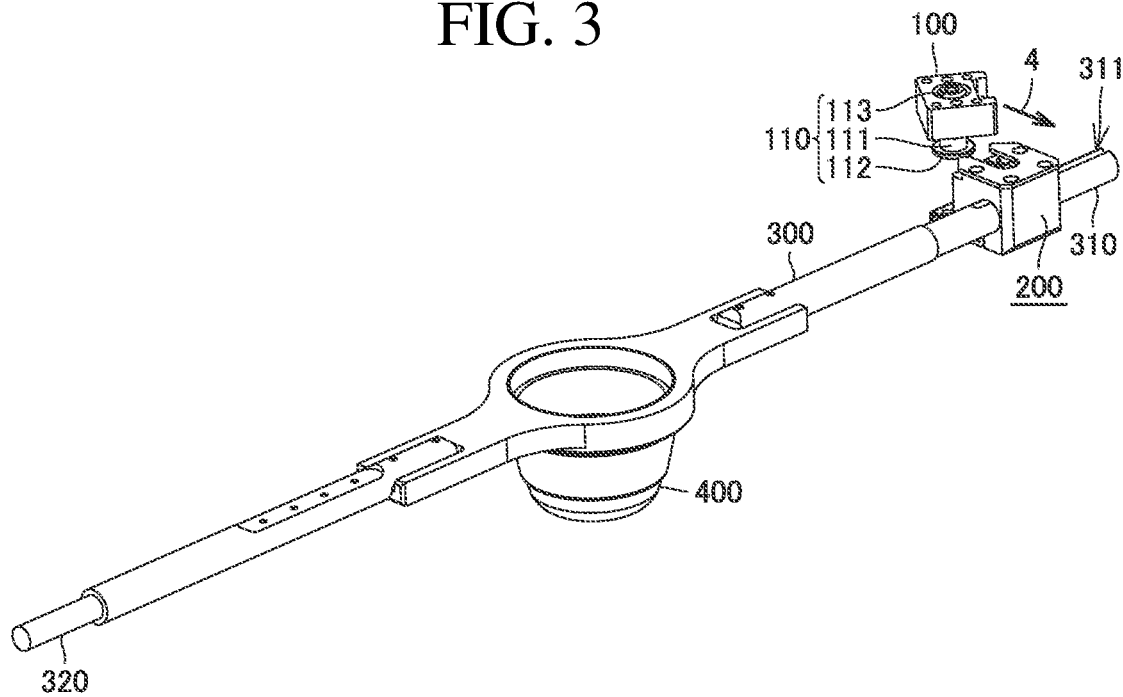
FIG. 3 is a perspective view showing the configuration of the compression tube attaching-detaching unit according to one embodiment of the present invention.

A compression tube attaching-detaching unit is provided at the front lower side of the imaging system 14. FIG. 3 is a perspective view showing the configuration of the compression tube attaching-detaching unit according to one embodiment of the present invention. As shown in FIG. 1 and FIG. 3, the compression tube attaching-detaching unit is provided with an arm 300, a connecting pin 110, and an attaching-detaching mechanism portion 200.

The arm 300 supports the compression tube 400. The attaching-detaching mechanism portion 200 is removably coupled with the connecting pin 110 to mount the arm 300 to the radiographic fluoroscopic imaging apparatus 10. Specifically, the connecting pin 110 is fixed to the housing 100. The housing 100 is connected to the lower portion of the front side of the imaging system 14. The attaching-detaching mechanism portion 200 is attached to the imaging system 14 via the connecting pin 110 and the housing 100.

The arm 300 is rotatable in the horizontal direction as indicated by the arrow 3 about the connecting pin 110 as a rotating shaft via the attaching-detaching mechanism portion 200. The rotation of the arm 300 causes the compression tube 400 to move between the inside of the X-ray field of view and the outside of the X-ray field of view of the imaging system 14.

At the end of the arm 300, a connecting portion 310 to be connected to the attaching-detaching mechanism portion 200 is provided. The connecting portion 310 is provided with an engaging groove 311 in which a setscrew attached to the main body of the attaching-detaching mechanism portion 200 to be described later is inserted.

At the end of the arm 300 opposite the attaching-detaching mechanism portion 200 side, an operation grip 320 for manually rotating the compression tube 400 is provided. The operation grip 320 is provided with a lock switch (not shown).

A compression tube 400 is attached to an intermediate portion of the arm 300. When performing fluoroscopic imaging while compressing the imaging target S by the compression tube 400, in a state in which the compression tube 400 is manually pressed against the imaging target S with the operation grip 320 held, the lock switch provided on the operation grip 320 is pressed to maintain the compression of the imaging target S by the compression tube 400. By pressing the lock switch again after completing the fluoroscopic imaging, the compression of the imaging target S is released by the compression tube 400.

Figure 4:
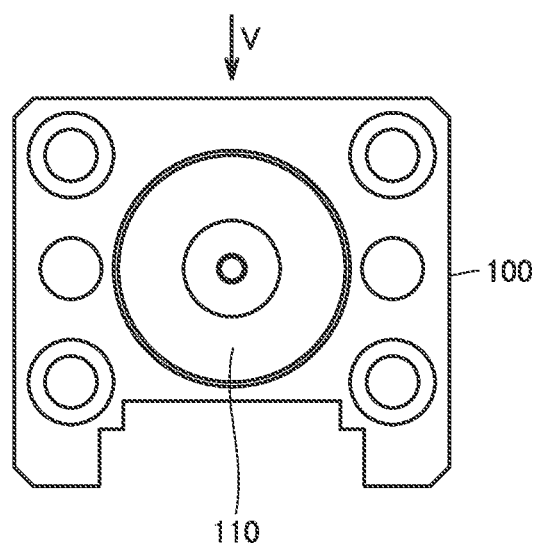
FIG. 4 is a plan view showing a state in which a connecting pin included in the compression tube attaching-detaching unit according to one embodiment of the present invention is fixed to a housing.
Figure 5:
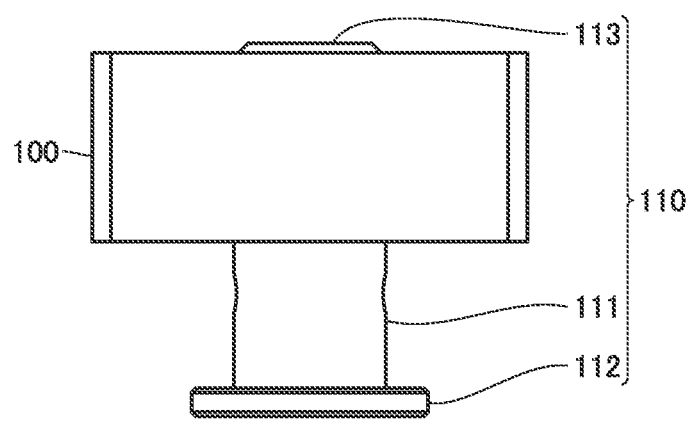
FIG. 5 is a side view of the housing and the connecting pin of FIG. 4 as viewed in the direction of the arrow V.
Figure 6:
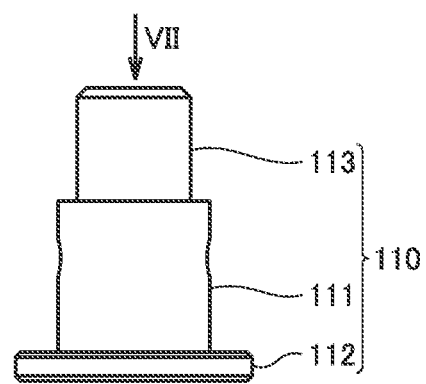
FIG. 6 is a side view showing the structure of the connecting pin included in the compression tube attaching-detaching unit according to one embodiment of the present invention.
Figure 7:
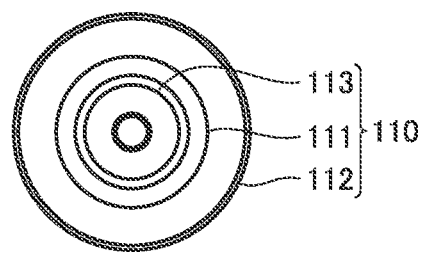
FIG. 7 is a plan view of the connecting pin of FIG. 6 as viewed from the arrow VII.

Hereinafter, the configuration of the compression tube attaching-detaching unit according to one embodiment of the present invention will be described in detail. FIG. 4 is a plan view showing the state in which the connecting pin included in the compression tube attaching-detaching unit according to one embodiment of the present invention is fixed to the housing. FIG. 5 is a side view of the housing and the connecting pin of FIG. 4 as viewed from the arrow V direction. FIG. 6 is a side view showing the structure of the connecting pin included in the compression tube attaching-detaching unit according to one embodiment of the present invention. FIG. 7 is a plan view of the connecting pin of FIG. 6 as viewed from the arrow VII direction.

As shown in FIG. 4 to FIG. 7, the connecting pin 110 has a shaft portion 111 and a flange portion 112 positioned at the tip end of the shaft portion 111. In this embodiment, each of the shaft portion 111 and the flange portion 112 has a cylindrical outer shape. However, the shape of each of the shaft portion 111 and the flange portion 112 is not limited to a cylindrical shape. It may be a columnar shape. The shaft portion 111 and the flange portion 112 are coaxially positioned.

The connecting pin 110 further has a reduced diameter portion 113 smaller in diameter than the shaft portion 111 on a side opposite to the flange portion 112 side of the shaft portion 111. In this embodiment, the reduced diameter portion 113 has a cylindrical outer shape. However, the shape of the reduced diameter portion 113 is not limited to a cylindrical shape. It may be a columnar shape. The shaft portion 111 and the reduced diameter portion 113 are coaxially positioned.

The housing 100 has a through-hole in which the reduced diameter portion 113 of the connecting pin 110 is inserted. The connecting pin 110 is fixed to the housing 100 with the reduced diameter portion 113 is inserted in the through-hole of the housing 100. With the connecting pin 110 fixed to the housing 100, each of the shaft portion 111 and the flange portion 112 is positioned below the housing 100.

Figure 8:
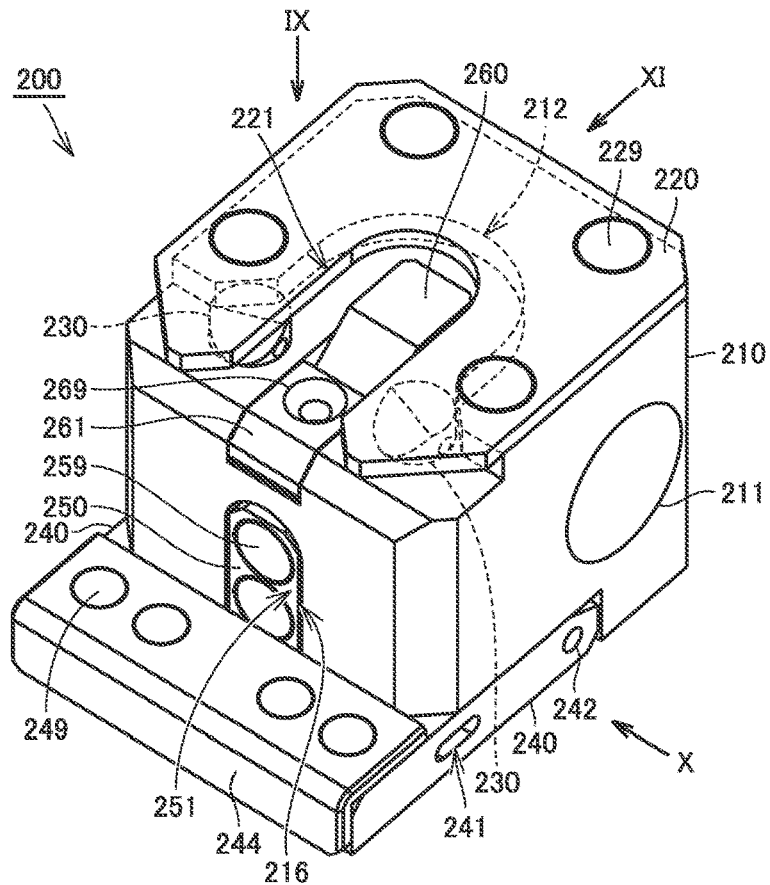
FIG. 8 is a perspective view showing the external appearance of the attaching-detaching mechanism portion included in the compression tube attaching-detaching unit according to one embodiment of the present invention.
Figure 9:
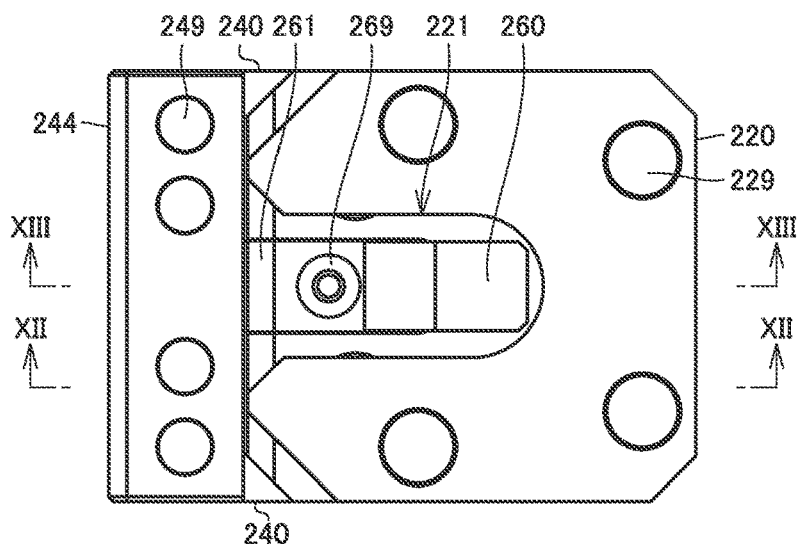
FIG. 9 is a plan view of the attaching-detaching mechanism portion as viewed from the direction of the arrow IX in FIG. 8.
Figure 10:
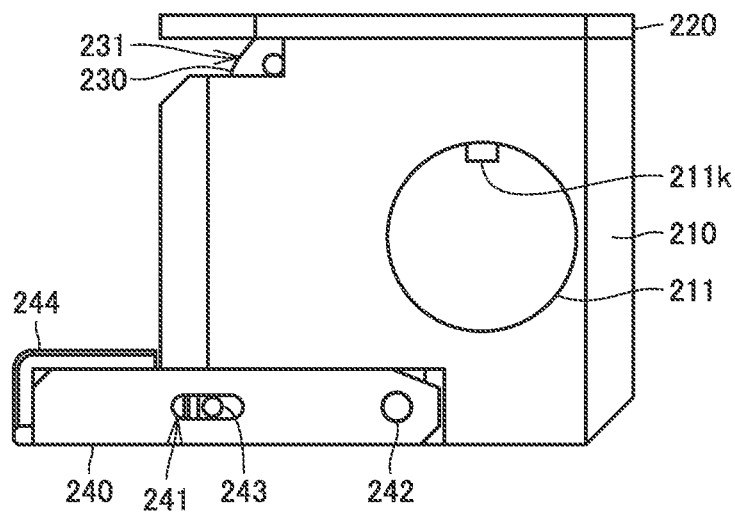
FIG. 10 is a side view of the attaching-detaching mechanism portion of FIG. 8 as viewed from the arrow X-direction in FIG. 8.
Figure 11:
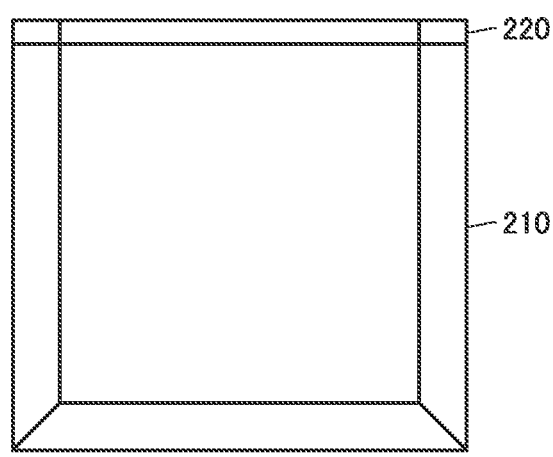
FIG. 11 is a rear view of the attaching-detaching mechanism portion of FIG. 8 as viewed from the arrow XI direction in FIG. 9.
Figure 12:
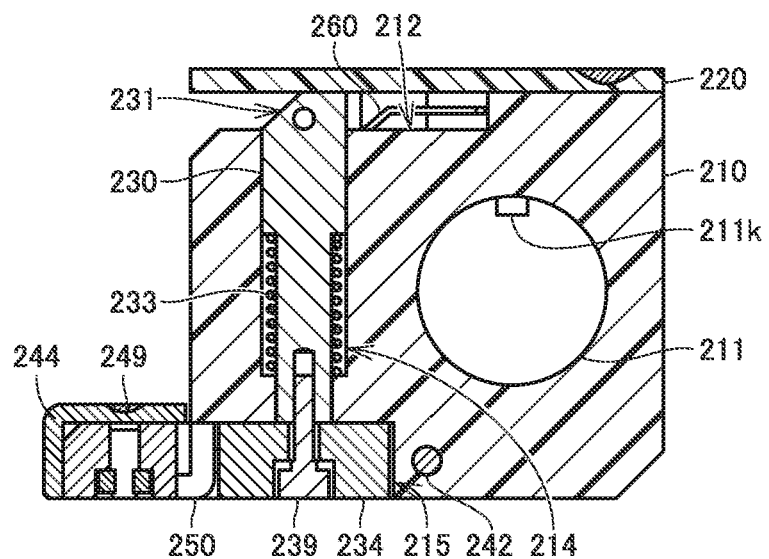
FIG. 12 is a cross-sectional view of the attaching-detaching mechanism portion of FIG. 9 as viewed from the XII-XII line arrow direction.
Figure 13:
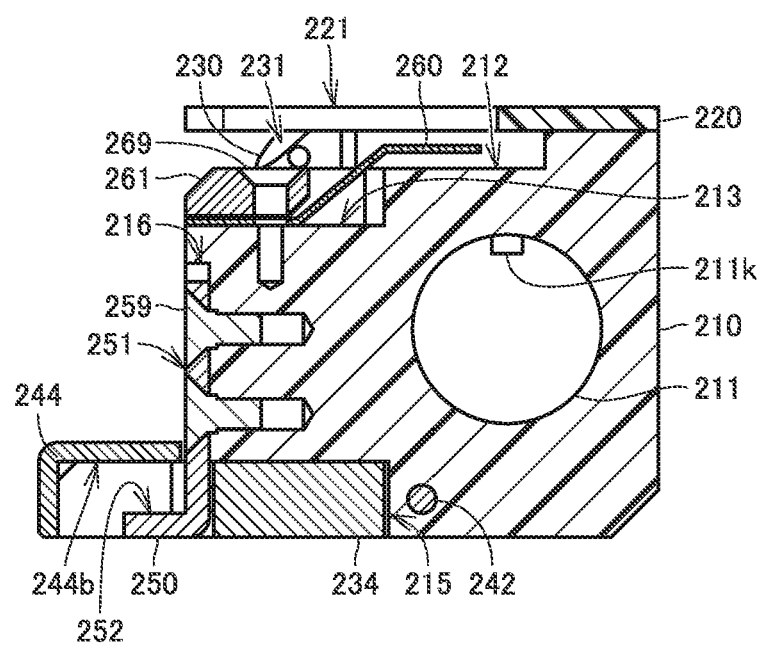
FIG. 13 is a cross-sectional view of the attaching-detaching mechanism portion of FIG. 9 as viewed from the XIII-XIII line arrow direction.

FIG. 8 is a perspective view showing the external appearance of the attaching-detaching mechanism portion included in the compression tube attaching-detaching unit according to one embodiment of the present invention. FIG. 9 is a plan view of the attaching-detaching mechanism portion of FIG. 8 as viewed from the arrow IX direction. FIG. 10 is a side view of the attaching-detaching mechanism portion of FIG. 8 as viewed from the arrow X direction. FIG. 11 is a rear view of the attaching-detaching mechanism portion of FIG. 8 as viewed from the arrow XI direction. FIG. 12 is a cross-sectional view of the attaching-detaching mechanism portion of FIG. 9 as viewed from the XII-XII line arrow direction. FIG. 13 is a cross-sectional view of the attaching-detaching mechanism portion of FIG. 9 as viewed from the XIII-XIII arrow direction.

As shown in FIG. 8 to FIG. 13, the attaching-detaching mechanism portion 200 includes a main body 210, a lid portion 220, a pair of lock pins 230 each serving as a locking portion, and a pair of unlock levers 240 each serving as an unlocking portion. In this embodiment, the attaching-detaching mechanism portion 200 further includes an elastic body 260.

The main body 210 has a substantially rectangular parallelepiped outer shape. The main body 210 is provided with a through-hole 211 into which the connecting portion 310 of the arm 300 is inserted. The through-hole 211 extends from the right side to the left side of the main body 210.

The main body 210 is provided with a setscrew 211k for securing the connecting portion 310 of the arm 300 inserted in the through-hole 211. In other words, the main body 210 is provided with a female thread that engages with the setscrew 211k. The tip end portion of the setscrew 211k protrudes inside the through-hole 211. The tip end portion of the setscrew 211k engages with the bottom surface of the engaging groove 311 of the connecting portion 310 of the arm 300 shown in FIG. 3, thereby securing the arm 300 to the main body 210.

As shown in FIG. 8, FIG. 12, and FIG. 13, at the upper surface of the main body 210, a groove portion 212 in which the flange portion 112 of the connecting pin 110 is relatively slidably inserted. The groove portion 212 has a U-shaped shape in which the front side of the main body 210 is open when viewed from a direction perpendicular to the upper surface of the main body 210. The width of the groove portion 212 is slightly larger than the diameter of the flange portion 112.

As shown in FIG. 13, at the upper portion of the front side of the main body 210, a deep groove portion 213 having a bottom surface below the bottom surface of the groove portion 212 is provided. The deep groove portion 213 has a U-shaped shape in which the front side of the main body 210 is open when viewed from a direction perpendicular to the upper surface of the main body 210. In the bottom surface of the deep groove portion 213, a downwardly extending female thread is provided.

As shown in FIG. 12, the main body 210 is provided with two stepped holes 214 in which a pair of lock pins 230 is inserted one by one. As shown in FIG. 12 and FIG. 13, in the lower surface of the front side of the main body 210, a recess 215 extending in the left-right direction so as to be continuous with the lower end of each of the two stepped holes 214 is provided.

As shown in FIG. 8 and FIG. 13, in front of the main body 210, at the central portion in the left-right direction, a U-shaped vertical groove portion 216 in which the lower surface side is open is provided. In the bottom surface of the vertical groove portion 216, two female threads that extend in the front-back direction are provided.

The main body 210 is made of a resin, such as, e.g., epoxy, or a metal, such as, e.g., stainless steel.

As shown in FIG. 8, FIG. 9, and FIG. 13, the lid portion 220 is constituted by a flat plate having a rectangular outer shape substantially similar to the upper surface of the main body 210. The lid portion 220 is provided with a cut-out portion 221 through which the shaft portion 111 of the connecting pin 110 is relatively slidably inserted. The cut-out portion 221 has a U-shape in which the front side of the lid portion 220 is open when viewed from a direction perpendicular to the upper surface of the lid portion 220. The central axis of the cut-out portion 221 of the lid portion 220 extending in the front-back direction substantially overlaps the central axis of the groove portion 212 of the main body 210 extending in the front-back direction.

The width of the cut-out portion 221 is slightly larger than the diameter of the shaft portion 111. At the front side end of the cut-out portion 221, the width of the cut-out portion 221 is widened in order to guide the shaft portion 111 to the inside of the cut-out portion 221. The lid portion 220 is made of metal, such as, e.g., stainless steel.

As shown in FIG. 8 and FIG. 9, the lid portion 220 is fixed to the upper surface of main body 210 by four screws 229. Consequently, as shown in FIG. 12 and FIG. 13, a space capable of accommodating the flange portion 112 of the connecting pin 110 is formed by the groove portion 212 of the lid portion 220 and the main body 210.

As shown in FIG. 12, each of the pair of lock pins 230, which are locking portions, is a stepped pin with a large-diameter portion and a small-diameter portion. An inclined surface 231 is provided at the end of the large-diameter portion. At the end portion of the small-diameter portion on a side opposite to the large-diameter portion, a female thread positioned at the central axis of the small-diameter portion is provided.

The lock pin 230 is inserted from the small-diameter portion side into the corresponding stepped hole 214 of the main body 210. The lock pin 230 is made of metal, such as, e.g., stainless steel.

A compression coil spring, which is a biasing member 233, is arranged so as to be sandwiched between the step portion of the stepped hole 214 and the step portion of the lock pin 230. The lock pin 230 receives an upward biasing force from the biasing member 233.

The pair of lock pins 230 is connected by a connecting block 234 arranged within the recess 215 of the main body 210 and headed screws 239. Specifically, the connecting block 234 is provided with two counter-bored holes penetrating in the up-down direction at the position corresponding to the female thread of the small-diameter portion of each of the pair of lock pins 230. The headed screw 239 inserted into the counter-bored hole of the connecting block 234 is threadedly engaged with the female thread of the small-diameter portion of the lock pin 230, thereby connecting the pair of lock pins 230 and the connecting block 234 to each other.

With the above-described configuration, as shown in FIG. 8, each of the pair of lock pins 230, which are locking portions, is attached to the main body 210 so as to be positioned on the slide insertion path of the flange portion 112 of the connecting pin 110 in a contactable and separatable manner with respect to the lid portion 220, and receives the biasing force in a direction toward the lid portion 220.

As shown in FIG. 8, FIG. 12, and FIG. 13, at the lid portion 220 side of each of the pair of lock pins 230, which is a locking portion, an inclined surface 231 that comes into slide contact with the flange portion 112 of the flange portion 112 of the connecting pin 110 to be slidably inserted is provided. The inclined surface 231 is inclined so as to be positioned in the slide insertion direction of the flange portion 112 as it advances toward the tip end of the lock pin 230. Note that the slide insertion direction of the flange portion 112 is a direction indicated by the arrow 4 in FIG. 3 and is substantially parallel to each of the central axes of the groove portion 212 of the main body 210 and the cut-out portion 221 of the lid portion 220.

Each of the inclined surfaces 231 of the pair of lock pins 230 is opposed to each other in an inclined manner. Specifically, when viewed from the axial direction of the lock pin 230, the ridge of the edge of the inclined surface 231 positioned at the upper end of the lock pin 230 is inclined so as to be positioned on the front side as it deviates from the central axis of the cut-out portion 221.

Since each of the inclined surfaces 231 of the pair of lock pins 230 is provided as described above, it is possible to adjust the relative positional relation between the connecting pin 110 and the attaching-detaching mechanism portion 200 so that the center of the flange portion 112 of the connecting pin 110 in contact with the inclined surface 231 of each of the pair of the inclined surfaces 231 is positioned on the central axis of the groove portion 212 of the main body 210.

As shown in FIG. 8 to FIG. 10, FIG. 12, and FIG. 13, each of the pair of unlock levers 240 as unlocking portions is rotatably mounted to the main body 210 about a rotating shaft 242 fixed to the side of the main body 210. The unlock lever 240 is made of metal, such as, e.g., stainless steel.

Each of the pair of unlock levers 240 extends in the front-rear direction. To the portion of each of the pair of unlock levers 240 positioned in front of the main body 210, a holding portion 244 is fixed by four screws 249. The holding portion 244 has an L-shaped outer shape in cross section. As shown in FIG. 13, an engagement surface 244b is exposed at the center of the inner top surface of the holding portion 244 in the left-right direction.

At each side of the pair of unlock levers 240, an elongated hole 241 extending in the front-rear direction is provided. In each of the elongated holes 241 of the pair of unlock levers 240, a corresponding connecting shaft 243 fixed one by one on both sides of the connecting block 234 is inserted. The connecting shaft 243 extends in the left-right direction.

In accordance with the movement of the connecting block 234 in the up-down direction together with a pair of lock pins 230, the unlock lever 240 is rotated about the rotating shaft 242 while the connecting shaft 243 moves in the front-rear direction within the elongated hole 241.

As shown in FIG. 8 and FIG. 13, the stopper 250 is attached to the vertical groove portion 216 of the main body 210. The stopper 250 has a mounting portion 251 extending in the up-down direction and a bent portion 252 bent forward from the lower end of the mounting portion 251. The mounting portion 251 of the stopper 250 is secured within the vertical groove portion 216 by two screws 259 threaded into female threads provided in the bottom surface of the vertical groove portion 216.

As shown in FIG. 13, the upper surface of the bent portion 252 of the stopper 250 serves as an engagement surface that engages with the engagement surface 244b of the holding portion 244 when the unlock lever 240 is rotated downward. When the engagement surface 244b and the engaging surface is engaged, the rotation of the unlock lever 240 is restricted.

With the above-described configuration, the unlocking portion separates the locking portion from the lid portion 220 against the biasing force of the biasing member 233. Specifically, by depressing the holding portion 244, the pair of unlock levers 240 are both rotated downward, and the connecting shaft 243 is lowered while moving in the elongated hole 241 toward the rotating shaft 242. Consequently, the pair of lock pins 230 is lowered against the biasing force of the biasing member 233.

In the left-right direction, because the distance between the rotating shaft 242 and the holding portion 244 are longer than the distance between the rotating shaft 242 and the connecting shaft 243, the holding portion 244 can be pushed down with less force by the principle of leverage.

As shown in FIG. 8, FIG. 9, FIG. 12, and FIG. 13, in this embodiment, a leaf spring, which is an elastic body 260, is attached to the main body 210 so as to be positioned in the groove portion 212. Note that the elastic body 260 is not limited to a leaf spring and may be a rubber or the like. It is not required that the elastic body 260 is provided.

Specifically, the leaf spring, which is an elastic body 260, has a mounting portion in contact with the bottom surface of the deep groove portion 213 of the main body 210, an inclined portion extending obliquely upward from the edge of the mounting portion, and a pressing portion extending along the bottom surface of the groove portion 212 from the tip of the inclined portion.

The leaf spring, which is an elastic body 260, is attached to the main body 210 in a state in which the mounting portion is sandwiched between the fixed block 261 arranged in the deep groove portion 213 of the main body 210 and the deep groove portion 213. Specifically, each of the fixed block 261 and the elastic body 260 is provided with a through-hole penetrating in the up-down direction. A screw 269 inserted through these through-holes is screwed with the female thread provided in the bottom surface of the deep groove portion 213. Thus, the leaf spring is secured to the main body 210.

With the leaf spring secured to the main body 210, the inclined portion of the leaf spring is spaced apart from the bottom surface of the groove portion 212 and is positioned on the slide insertion path of the flange portion 112 of the connecting pin 110.

When the flange portion 112 of the connecting pin 110 is slidably inserted, the inclined portion of the leaf spring is pushed down by the flange portion 112, and the pressing portion of the leaf spring is brought into contact with the lower surface of the flange portion 112. In this state, the flange portion 112 is biased toward the lid portion 220 by the leaf spring.

With the above-described configuration, the elastic body 260 biases the flange portion 112 of the connecting pin 110 accommodated between the main body 210 and the lid portion 220 toward the lid portion 220 side.

Figure 14:
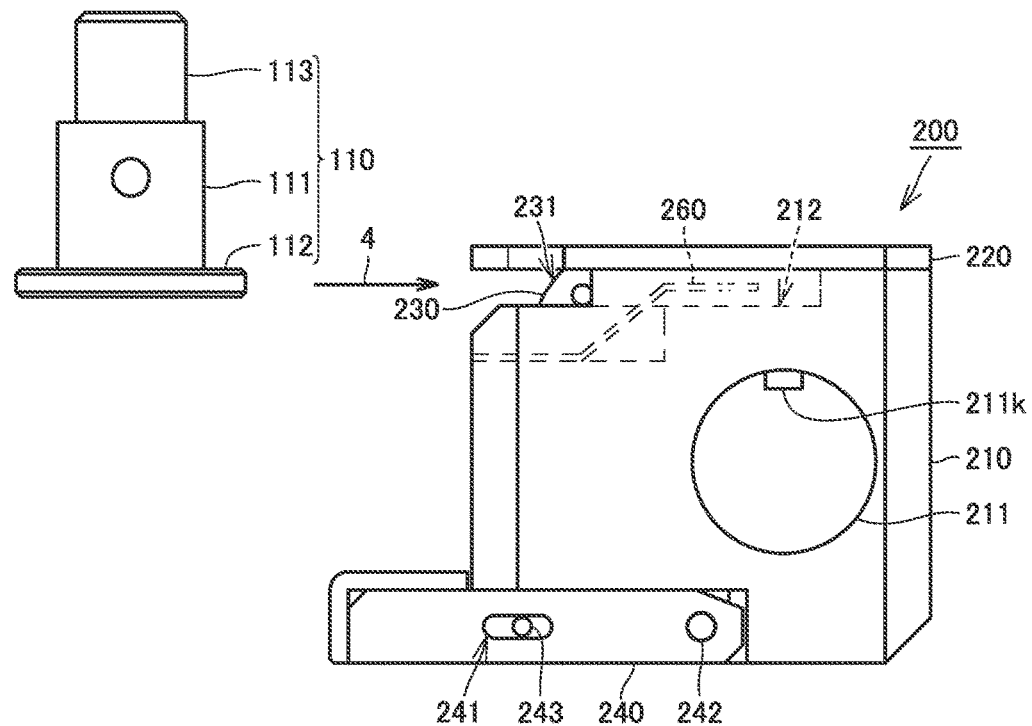
FIG. 14 is a side view showing a state in which in the compression tube attaching-detaching unit according to one embodiment of the present invention, the connecting pin is approached the attaching-detaching mechanism portion.

Hereinafter, the attaching and detaching operation of the compression tube attaching-detaching unit according to one embodiment of the present invention will be described. FIG. 14 is a side view showing a state in which in the compression tube attaching-detaching unit according to one embodiment of the present invention, the connecting pin is being approached to the attaching-detaching mechanism portion. As shown in FIG. 3 and FIG. 14, when connecting the connecting pin 110 and the attaching-detaching mechanism portion 200, the connecting pin 110 is slidably moved in a direction relatively approaching the attaching-detaching mechanism portion 200 as indicated by the arrow 4.

Figure 15:
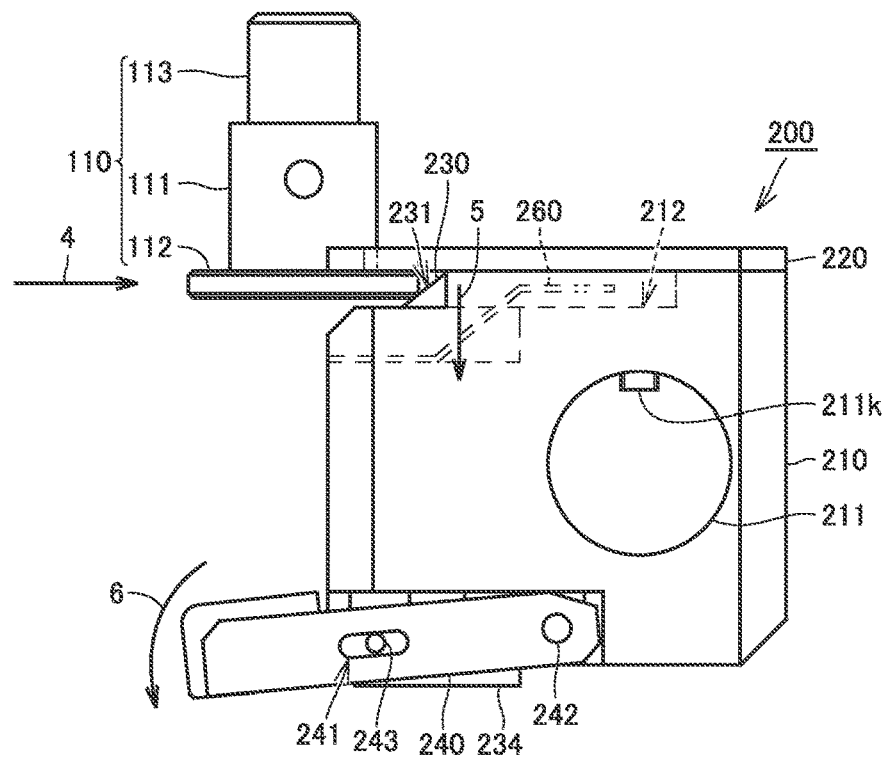
FIG. 15 is a side view illustrating a state in which, in the compression tube attaching-detaching unit according to one embodiment of the present invention, the flange portion of the connecting pin is in contact with the inclined surface of the locking portion to press down the locking portion.

FIG. 15 is a side view illustrating a state in which in the compression tube attaching-detaching unit according to one embodiment of the present invention, the flange portion of the connecting pin is pushing down the locking portion by pressing the inclined surface of the locking portion.

As shown in FIG. 15, by pressing the inclined surface 231 of the lock pin 230, the flange portion 112 of the connecting pin 110 pushes down the lock pin 230 against the biasing force of the biasing member 233 as indicated by the arrow 5. Thus, the unlock lever 240 is rotated downward as indicated by the arrow 6.

Figure 16:
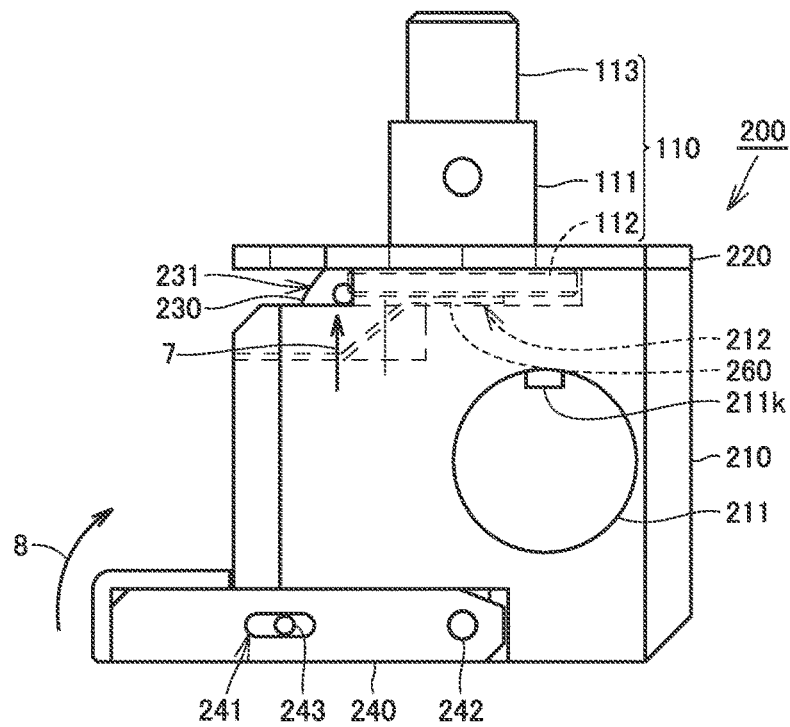
FIG. 16 is a side view showing a state in which in the compression tube attaching-detaching unit according to one embodiment of the present invention, the connecting pin is connected to the attaching-detaching mechanism portion.

FIG. 16 is a side view showing a state in which in the compression tube attaching-detaching unit according to one embodiment of the present invention, the connecting pin is connected to the attaching-detaching mechanism portion. As shown in FIG. 16, in a state in which the connecting pin 110 is coupled with the attaching-detaching mechanism portion 200, the flange portion 112 of the connecting pin 110 is housed between the main body 210 and the lid portion 220, and the lock pin 230 is, as indicated by the arrow 7, raised by the biasing force of the biasing member 233 and is in contact with the lid portion 220. Thus, the unlock lever 240 is rotated upward as indicated by the arrow 8.

In this state, the inclined surface 231 is not positioned on the flange portion 112 side of the lock pin 230. Therefore, the force for depressing the lock pin 230 does not work even when the lock pin 230 and the flange portion 112 are brought into contact with each other. Thus, the connecting pin 110 is maintained in a state of being connected to the attaching-detaching mechanism portion 200 by the lock pin 230 as a locking portion.

Further, in this state, the elastic body 260 presses the flange portion 112 of the connecting pin 110 against the lid portion 220, and therefore, it is possible to stabilize the connection posture between the connecting pin 110 and the attaching-detaching mechanism portion 200.

Figure 17:
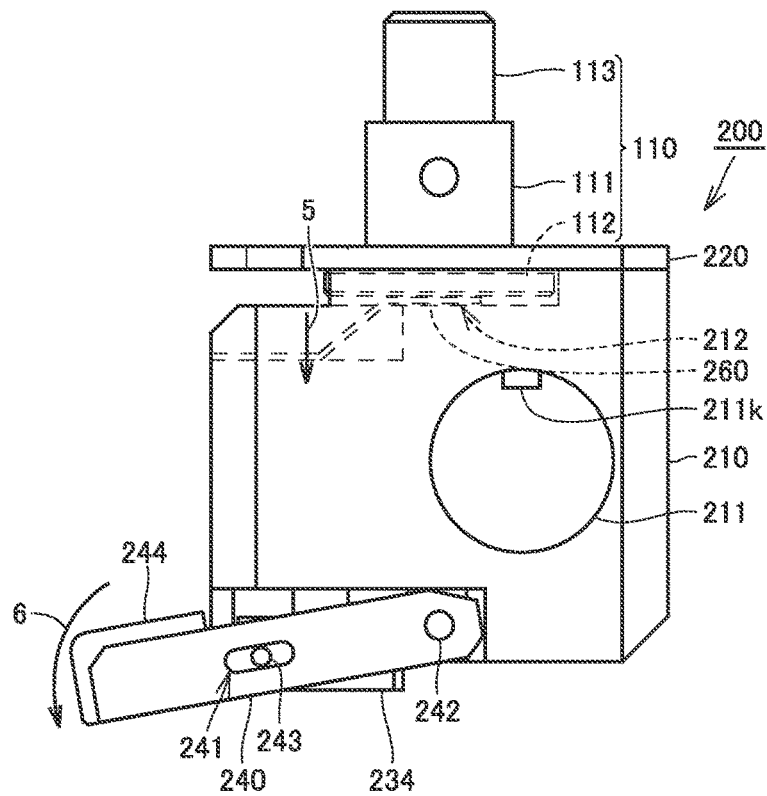
FIG. 17 is a side view illustrating a state in which in the compression tube attaching-detaching unit according to one embodiment of the present invention, the unlocking portion is rotated downward in order to remove the connecting pin from the attaching-detaching mechanism portion.

FIG. 17 is a side view illustrating a state in which in the compression tube attaching-detaching unit according to one embodiment of the present invention, the unlocking portion is rotated downward in order to remove the connecting pin from the attaching-detaching mechanism portion.

As shown in FIG. 17, by rotating the unlock lever 240 downward by pushing down the holding portion 244 as indicated by the arrow 6, the lock pin 230 is lowered against the biasing force of the biasing member 233 as indicated by the arrow 5. With this, the lock by the locking portion is released.

Figure 18:
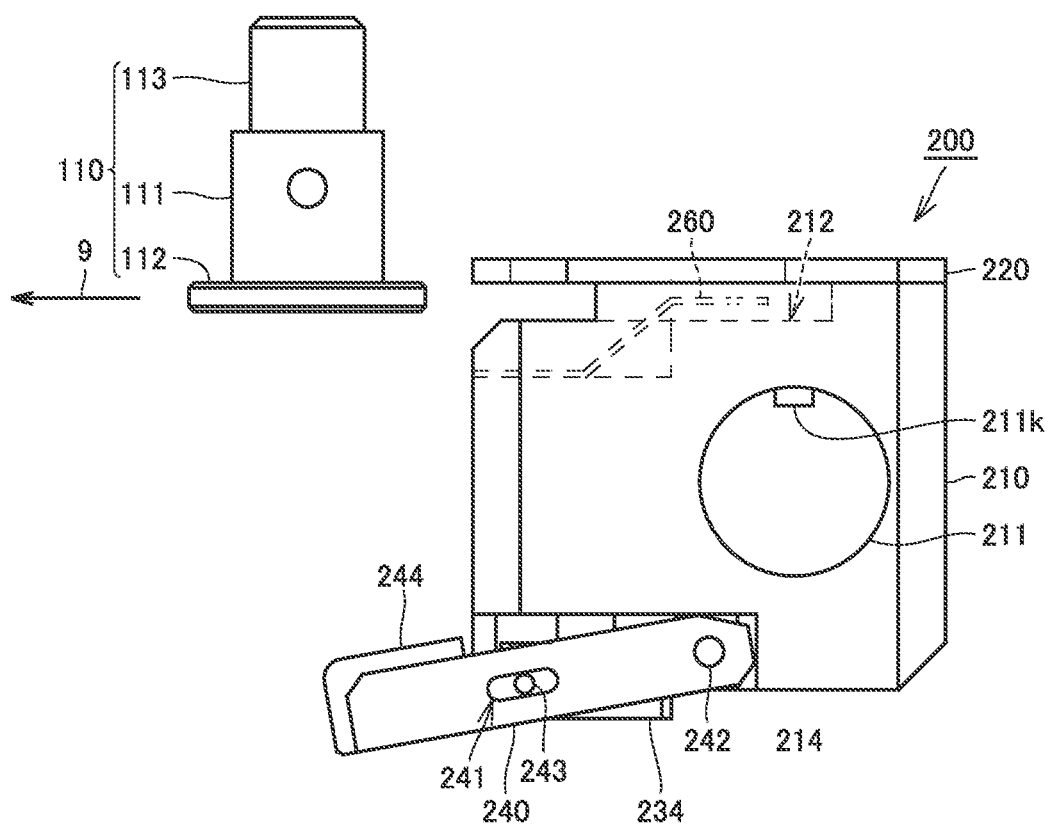
FIG. 18 is a side view showing a state in which in the compression tube attaching-detaching unit according to one embodiment of the present invention, the connecting pin has been removed from the attaching-detaching mechanism portion.

FIG. 18 is a side view showing a state in which in the compression tube attaching-detaching unit according to one embodiment of the present invention, the connecting pin is removed from the attaching-detaching mechanism portion. As shown in FIG. 18, in a state in which the lock is released by the locking portion, by slidably moving the connecting pin 110 in a direction relatively separating from the attaching-detaching mechanism portion 200 as indicated by the arrow 9, the connection between the connecting pin 110 and the attaching-detaching mechanism portion 200 is released.

Figure 19:
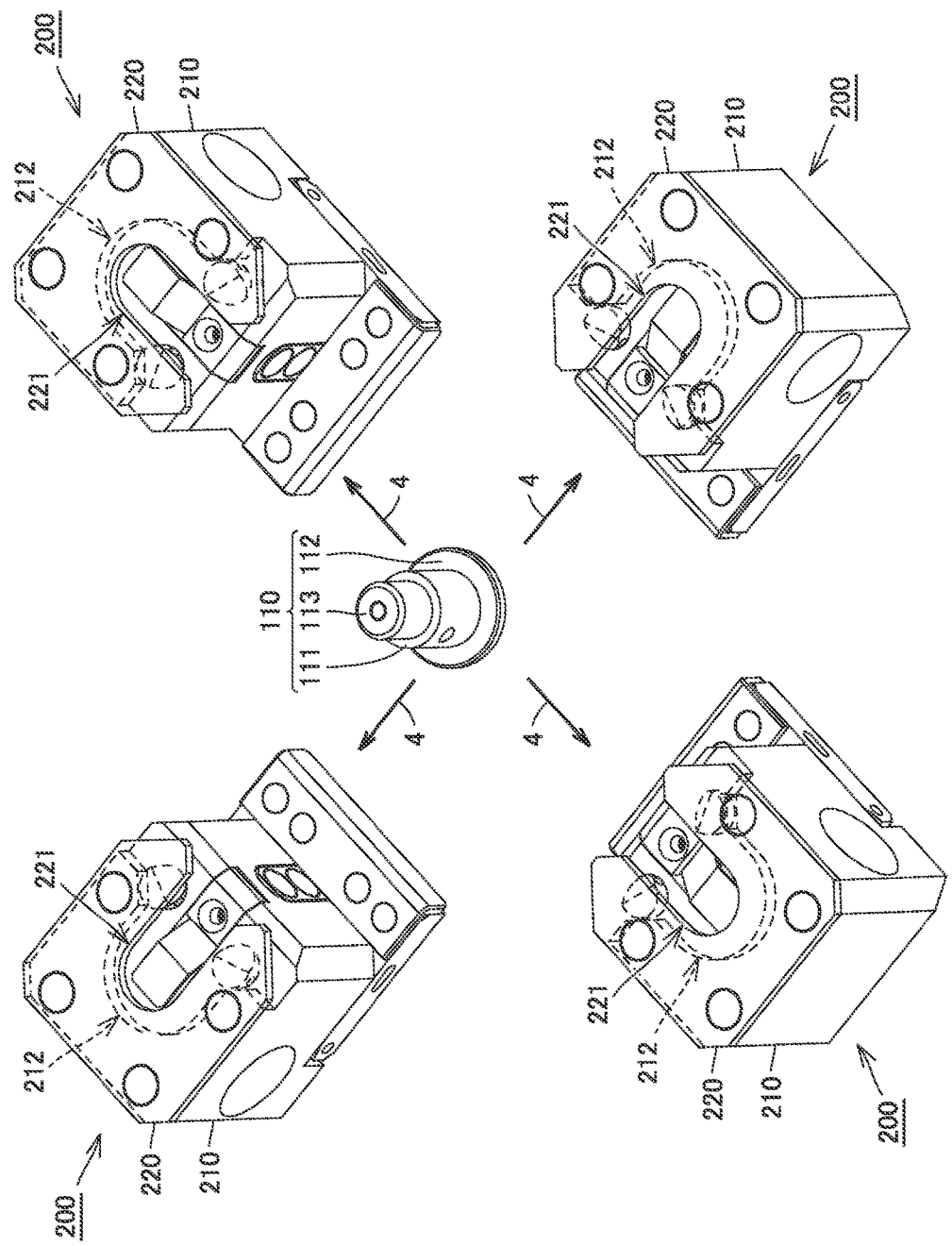
FIG. 19 is a perspective view illustrating the sliding insertion direction of the connecting pin relative to the attaching-detaching mechanism portion in the compression tube attaching-detaching unit according to one embodiment of the present invention.

FIG. 19 is a perspective view illustrating the sliding direction of the connecting pin relative to the attaching-detaching mechanism portion in the compression tube attaching-detaching unit according to one embodiment of the present invention.

As shown in FIG. 19, in the compression tube attaching-detaching unit according to one embodiment of the present invention, since each of the shaft portion 111 and the flange portion 112 of the connecting pin 110 has a cylindrical outer shape, in any direction of 360°, the connecting pin 110 can be attached to the attaching-detaching mechanism portion 200 by sliding the connecting pin 110 in a direction relatively approaching the attaching-detaching mechanism portion 200.

In the compression tube attaching-detaching unit according to one embodiment of the present invention, the attaching-detaching mechanism portion 200 includes the main body 210, the lid portion 220, the locking portion, and the unlocking portion described above. Therefore, the connecting pin 110 can be connected to the attaching-detaching mechanism portion 200 by sliding the connecting pin 110 in a direction relatively approaching the attaching-detaching mechanism portion 200. The connection of the connecting pin 110 can be released by sliding the connecting pin 110 in a direction relatively separating from the attaching-detaching mechanism portion 200 in a state in which the unlocking portion is rotated. Therefore, it is possible to easily attach and detach the connecting pin 110 to and from the attaching-detaching mechanism portion 200. As a result, the compression tube 400 can be easily attached and detached.

Further, the arm 300 is rotatable about the connecting pin 110 as a rotating shaft via the attaching-detaching mechanism portion 200. This allows the compression tube 400 to be easily moved between the inside of the X-ray field of view and the outside of the X-ray field of view in the imaging system 14.

Further, at the end portion of the arm 300 opposite to the attaching-detaching mechanism portion 200 side, an operation grip 320 for manually rotating the compression tube 400 is provided. With this, the force pressing the compression tube 400 to the imaging target S can be finely adjusted as compared with the case in which motor power assist is used. As a result, it is possible to prevent excessive pressure application of the compression tube 400.

Further, the attaching-detaching mechanism portion 200 is further provided with the elastic body 260 mounted on the main body 210 to be positioned within the groove portion 212 to bias the flange portion 112 accommodated between the main body 210 and the lid portion 220 toward the lid portion 220. With this, the connecting pin 110 can be stably connected to the attaching-detaching mechanism portion 200. As a result, the compression tube 400 can be stably supported.

The embodiment disclosed herein is to be considered in all respects as illustrative and not restrictive. The scope of the present invention is indicated by the appended claims rather than by the foregoing description and is intended to include all modifications within the meanings and ranges equivalent to the scope of the claims.

DESCRIPTION OF SYMBOLS

10: Radiographic fluoroscopic imaging apparatus
11: Bed
12: Column unit
13: Flame
14: Imaging system
15: Operation handle
100: Housing
110: Connecting pin
111: Shaft portion
112: Flange portion
113: Reduced diameter portion
200: Attaching-detaching mechanism portion
210: Main body
211: Through-hole
211k: Setscrew
212, 213: Groove portion
214: Stepped hole
215: Recess
216; Vertical groove portion
220: Lid portion
221: Cut-out portion
229, 249, 259, 269: Screw
230: Lock pin
231: Inclined surface
233: Biasing member
234: Connecting block
239: Headed screw
240: Unlock lever
241: Elongated hole
242: Rotating shaft
243: Connecting shaft
244: Holding portion
244b: Engagement surface
250; Stopper
251: Mounting portion
252: Bent portion
260: Elastic body
261: Fixed block
300: Arm
310: Connecting portion
311: Engaging groove
320: Operation grip
400: Compression tube
2000: Special Disclosure
S: Imaging target

The invention claimed is:

1. A compression tube attaching-detaching unit comprising:
an arm configured to support a compression tube;
a connecting pin; and
an attaching-detaching mechanism portion configured to mount the arm on a radiographic fluoroscopic imaging apparatus by being detachably coupled with the connecting pin,
wherein the connecting pin has a shaft portion and a flange portion positioned at a tip end of the shaft portion,
wherein the attaching-detaching mechanism portion includes:
a main body having a groove portion into which the flange portion is relatively slidably inserted;
a lid portion having a cut-out portion into which the shaft portion is relatively slidably inserted, the lid portion being fixed to the main body to accommodate the flange portion between the lid portion and the main body;
a locking portion attached to the main body to be positioned on a slide insertion path of the flange portion, the locking portion being provided so as to be contactable and separatable with respect to the lid portion and being configured to receive a biasing force in a direction approaching the lid portion; and
an unlocking portion attached to the main body, the unlocking portion being configured to separate the locking portion from the lid portion against the biasing force,
wherein an inclined surface that comes into slide contact with the flange portion is provided at a lid portion side of the locking portion, and
wherein the inclined surface is inclined to be positioned in a slide insertion direction of the flange portion as the inclined surface advances toward a tip end of the locking portion.

2. The compression tube attaching-detaching unit as recited in claim 1,
wherein the shaft portion and the flange portion each have a cylindrical outer shape.

3. The compression tube attaching-detaching unit as recited in claim 1,
wherein the attaching-detaching mechanism portion further includes an elastic body attached to the main body to be positioned within the groove portion, the elastic body being configured to bias the flange portion toward the lid portion.

4. The compression tube attaching-detaching unit as recited in claim 2,
wherein the arm is rotatable via the attaching-detaching mechanism portion about the connecting pin as a rotating shaft.

5. The compression tube attaching-detaching unit as recited in claim 4,
   wherein at an end portion of the arm opposite to an attaching-detaching mechanism portion side of the arm, an operation grip for manually rotating the compression tube is provided.

\* \* \* \* \*